United States Patent [19]

Miyadera et al.

[11] 4,147,863

[45] Apr. 3, 1979

[54] 7-D-(−)-MANDELAMIDO-3-(1-METHYL-1H-TETRAZOL-5-YL)VINYL-3-CEPHEM-4-CARBOXYLIC ACID

[75] Inventors: Tetsuo Miyadera; Mitsuo Nagano; Shinichi Sugawara, all of Tokyo, Japan

[73] Assignee: Sankyo Company Limited, Tokyo, Japan

[21] Appl. No.: 607,690

[22] Filed: Aug. 25, 1975

[30] Foreign Application Priority Data

Sep. 4, 1974 [JP] Japan .................................. 49-101693

[51] Int. Cl.$^2$ ........................................... C07C 501/60
[52] U.S. Cl. ..................................... 542/436; 542/444; 542/402
[58] Field of Search ..................... 260/240 E, 243 C; 542/436, 444

[56] References Cited

U.S. PATENT DOCUMENTS

| | | | |
|---|---|---|---|
| 3,129,224 | 4/1964 | Collins | 260/243 C |
| 3,352,858 | 11/1967 | Crast et al. | 260/243 C |
| 3,719,672 | 3/1973 | Heusler et al. | 260/243 C |
| 3,719,673 | 3/1973 | Bickel et al. | 260/243 C |
| 3,769,277 | 10/1973 | Long et al. | 260/243 C X |
| 3,840,535 | 10/1974 | Kaplan et al. | 260/243 C |
| 3,867,379 | 2/1975 | Dolfini et al. | 260/243 C |
| 3,919,206 | 11/1975 | Patchornek | 260/243 C |
| 3,932,397 | 1/1976 | Breuer et al. | 260/243 C |
| 3,962,232 | 6/1976 | Koppel | 260/243 C |

*Primary Examiner*—Allen B. Curtis
*Attorney, Agent, or Firm*—Flynn & Frishauf

[57] ABSTRACT

Novel cephalosporin derivatives having a (1-alkyl-1H-tetrazol-5-yl)vinyl group at the 3-position of the cephem nucleus and showing an excellent antibacterial activity are disclosed. A process for preparing the cephalosporin derivatives is also disclosed.

1 Claim, No Drawings

7-D-(−)-MANDELAMIDO-3-(1-METHYL-1H-TETRAZOL-5-YL)VINYL-3-CEPHEM-4-CARBOXYLIC ACID

This invention relates to novel cephalosporin derivatives having the following formula and their salts:

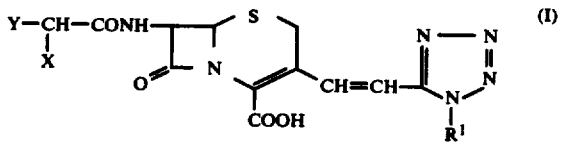

in which $R^1$ represents a lower alkyl group, Y represents a phenyl, thienyl, cyanomethylthio or isoxazolylthio group, and X represents hydrogen atom or hydroxyl group. Further, this invention relates to a process for preparing the above-mentioned cephalosporin derivatives.

In the above-mentioned formula (I), $R^1$ represents a lower alkyl group, preferably an alkyl group having 1–4 carbon atoms such as methyl, ethyl, n-propyl, isopropyl, n-butyl and isobutyl.

A compound having the formula (I) may be converted into a pharmaceutically acceptable salt. As the pharmaceutically acceptable salt, there may be mentioned a non-toxic salt, preferably an alkali metal salt such as a sodium salt.

All of cephalosporin derivatives having the formula (I) and their salts which are provided by the present invention are novel compounds, and are of value as pharmaceuticals due to their excellent antibacterial activity.

A number of cephalosporin-type compounds having antibacterial activity have heretofore been known. Some of them have been employed in practice as pharmaceuticals. Recently, compounds having a vinyl group at the 3-position of the cephem nucleus were synthesized and tested for their antibacterial activity. For instance, there are disclosed cephalosporin derivatives having a vinyl group at the 3-position in Japanese Provisional Patent Publication No. 2678/71. Yet, it does not appears that these known compounds have sufficiently satisfactory antibacterial activity against a wide variety of gram-positive and gram-negative bacteria. Hence, said type of cephalosporin compounds have not yet been used in practice as pharmaceuticals.

As a result of research for the purpose of finding compounds having an excellent antibacterial activity out of the above-mentioned type of the compounds, the present inventors have now found that the compounds having the aforementioned formula (I) show an excellent antibacterial activity not only superior to the previously known 3-vinylcephalosporin-type compounds but also similar or superior to the cephalosporin derivatives now used practically, and have attained the present invention.

It is, accordingly, a primary object of this invention to provide new cephalosporin compounds (I) having an excellent antibacterial activity.

Other objects of this invention will be apparent from the following description.

Compounds having the formula (I) which are provided by the present invention show an excellent antibacterial activity against a wide variety of bacteria. The results of test for the antibacterial activity are set out in the following Table.

Table

| Compound | Minimal Inhibitory Concentrations mcg/ml | | | | |
|---|---|---|---|---|---|
| | I | II | III | IV | V |
| 7-Thienylacetamido-3-5-yl)vinyl-3-cephem-4-carboxylic acid | 0.025 | 0.4 | 0.4 | 0.4 | 0.4 |
| 7-Cyanomethylthioacetamido-(1-methyl-1H-tetrazol-5-yl)vinyl-3-cephem-4-carboxylic acid | 0.05 | 0.8 | 0.8 | 1.5 | 6.2 |
| 7-D(-)-Mandelamido-3-(1-methyl-1H-tetrazol-5-yl)vinyl-3-cephem-4-carboxylic acid | 0.05 | 0.1 | 0.05 | 0.4 | 0.05 |
| 7-(3-Isoxazolylthio)acetamido-3-(1-methyl-1H-tetrazol-5-yl)-vinyl-3-cephem-4-carboxylic acid | ≦0.1 | 0.4 | 0.8 | 0.8 | 50 |
| Comparative compound | | | | | |
| Cephalothin | 0.05 | 6.2 | 12.5 | 6.2 | 6.2 |
| Cefazolin | 0.1 | 0.8 | 1.5 | 0.8 | 12.5 |
| Cefamandole | ≦0.1 | 0.8 | 0.4 | 0.8 | 0.8 |

I:*Staphylococcus aureus* 209 P
II:*Escherichia coli* NIHJ
III:*Shigella flexneri* 2a
IV:*Klebsiella* 806
V:*Proteus vulgaris*

Therefore, the compounds of the formula (I) are of value as pharmaceuticals for treating bacterial diseases. For this purpose, these compounds may be administered parenterally through intravenous or intramuscular injection or orally in the form of tablets, granules, capsules, syrup and the like. The dosage to be administered may vary depending upon condition, age, weight, administration procedure and the like, and a dosage of about 250–3000 mg per day is usually given to an adult at once or in the form of being divided into several portions.

The compounds of the formula (I) are exemplified as follows:

(1) 7-(2-Thienylacetamido)-3-(1-methyl-1H-tetrazol-5-yl)vinyl-3-cephem-4-carboxylic acid,
(2) 7-Cyanomethylthioacetamido-3-(1-methyl-1H-tetrazol-5-yl)vinyl-3-cephem-4-carboxylic acid,
(3) 7-(3-Isoxazolylthio)acetamido-3-(1-methyl-1H-tetrazol-5-yl)vinyl-3-cephem-4-carboxylic acid, and
(4) 7-D(−)-Mandelamido-3-(1-methyl-1H-tetrazol-5-yl)vinyl-3-cephem-4-carboxylic acid.

Particularly, the compound (4) is most preferred in view of the antibacterial activity.

The compound of the formula (I) is obtained by reacting a compound of the formula

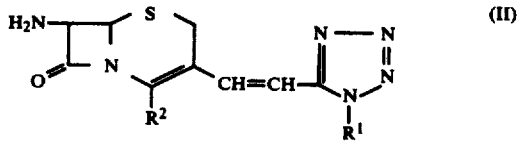

with a carboxylic acid of the formula

or its reactive derivative to prepare a compound of the formula

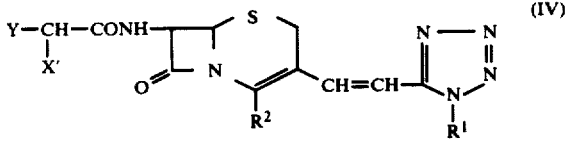

and, in case X' is a protected hydroxyl group and/or $R^2$ is a protected carboxyl group, further subjecting the resulting compound to the reaction for removing the protecting groups.

In the above-mentioned formulae, $R^1$ and Y have the same meanings as defined hereinbefore.

X' represents hydrogen atom or a protected hydroxyl group. There is no specific limitation on the protecting group of the hydroxyl group, so far as it does not affect another moiety of the compound while the reaction for removal of the protecting group shall be performed later on. Such a protecting group may preferably be a halogenoacetyl group, for instance, dichloroacetyl and tetrahydropyranyl group.

$R^2$ represents a carboxyl or protected carboxyl group. There is no specific limitation on the protecting group employed, so far as it is included in the protecting groups ordinarily employed in the procedure for preparing cephalosporin or penicillin derivatives. The protection of the carboxyl group may be effected by converting the carboxyl group into an ester with the corresponding protecting agent.

The protecting group forming an ester may be exemplified by a benzhydryl group, a tertiary lower alkyl group such as tert-butyl and tert-amyl, a phenacyl group which may have substituents on the aromatic ring such as phenacyl and p-bromophenacyl, a halogenoalkyl group such as 2,2,2-trichloroethyl, an alkoxyalkyl group such as methoxymethyl, a benzyl group which may have substituents on the aromatic ring such as benzyl and p-methoxybenzyl, and a trialkylsilyl group such as trimethylsilyl. The most preferable protecting group is benzhydryl. As a protecting group other than the ester-forming protecting group, there may be mentioned a group capable of forming an acid amide, for instance, o-benzosulphimido group.

In the process of the present invention, the reaction between a compound of the formula (II) and a carboxylic acid of the formula (III) or its reactive derivative to prepare a compound of the formula (IV) may be carried out in the presence of an inactive solvent. There is no specific limitation on the solvent employed, so far as it does not participate in the reaction. Such a solvent may be exemplified by a halogenated hydrocarbon, e.g., chloroform, dichloromethane and dichloroethane, a ketone, e.g., acetone and methyl ethyl ketone, an ether, e.g., diethyl ether and tetrahydrofuran, a nitrile, e.g., acetonitrile and an ester, e.g., ethyl formate and ethyl acetate. Further, mixtures of these organic solvents and water may be mentioned.

The carboxylic acid of the formula (III) may be exemplified by thienylacetic acid, cyanomethylthioacetic acid, isoxazolylthioacetic acid and O-dichloroacetylmandelic acid. In the process of this invention, these carboxylic acids may be employed in the form of either free acids or reactive derivatives. As the reactive derivative there may be mentioned an acid halide, an acid anhydride, a mixed acid anhydride, a reactive amide and an acid azide of the carboxylic acid. The acid halide may be exemplified by a chloride and bromide of the carboxylic acid, for instance, thienylacetyl chloride, cyanomethylthioacetyl chloride and O-dichloroacetylmandeloyl chloride. The mixed acid anhydride may be an anhydride of the carboxylic acid with an alkylphosphoric acid, an alkylcarbonic acid or an aliphatic carboxylic acid, for instance, thienylacetyl ethylcarbonic anhydride, cyanomethylthioacetyl isobutylcarbonic anhydride, O-dichloroacetylmandelic ethylcarbonic anhydride, thienylacetyl pivaolyl anhydride and cyanomethylthioacetyl pivaloyl anhydride. The acid anhydride may be exemplified by thienylacetic anhydride and cyanomethylthioacetic anhydride. The reactive amide may be an amide derived from the carboxylic acid and triazole or imidazole. The acid azide may be an azide of the carboxylic acid, for instance, thienylacetylazide, cyanomethylthioacetylazide and O-tetrahydropyranylmandeloylazide.

The present reaction is performed by bringing the reactive derivative of the carboxylic acid of the formula (III) into contact with a starting compound of the formula (II) in the aforementioned inactive solvent. In case the reactive derivative is the acid halide, an acid-binding agent such as a bicarbonate or carbonate of an alkali metal, e.g., sodium hydrogencarbonate and sodium carbonate, and an organic base, e.g., triethylamine, pyridine and dimethylaniline may be present in the reaction system. In the case of other reactive derivatives, the above-mentioned base may be or may not be present in the reaction system.

There is no specific limitation on the reaction temperature, but relatively low temperatures are preferably adopted so as to avoid side-reactions. Ordinarily, the reaction temperature is between −10° C. and room temperature. The reaction time varies mainly depending on the reaction temperature, kind of the starting compounds and the like. Generally, the period of time is between about 30 minutes and 2 hours.

In case the carboxylic acid of the formula (III) is involved, the reaction is carried out in the presence of a condensing agent such as N,N'-dicyclohexylcarbodiimide and N,N'-diethylcarbodiimide.

After completion of the reaction, the desired compound of the formula (IV) is taken out of the reaction mixture in the conventional manner. For instance, after the reaction, an organic solvent immiscible with water is added to the reaction mixture, and, after washing with water, the solvent was distilled off to leave the desired compound. The desired compound thus obtained may be further purified, if necessary, by the conventional method such as recrystallization reprecipitation and chromatography.

By the above-mentioned reaction, the desired compound of the formula (I) is obtained if $R^2$ of the starting compound is a carboxyl group. However, if the said $R^2$ is a protected carboxyl group, the resulting compound of the formula (IV) shall be converted into the desired compound of the formula (I) through reaction for removal of the protecting group in the conventional manner. The present reaction for removal of the protecting group may be carried out through reduction or treatment with an acid or a base. As a preferably reducing process employed in the case of involving the protecting group forming an ester such as benzyl and p-bromophenacyl, there may be mentioned a chemically reducing method such as employing a metal and an acid, e.g., zinc-acetic acid. In order to remove the protecting group forming an ester by treating with an acid, the compound of the formula (IV) is brought into contact with, for instance, trifluoroacetic acid or an acid as strong as the said acid in the presence or absence of an appropriate organic solvent. The acid to be employed may be, for instance, trifluoroacetic acid or trichloroacetic acid. Trichloroacetic acid is most preferred. There is no specific limitation on the solvent, so far as it does not participate in the reaction. As the solvent, there may be mentioned a halogenated hydrocarbon such as chloroform, dichloromethane and dichloroethane, and an aromatic hydrocarbon such as benzene, toluene, chlorobenzene and anisole. Dichloroethane and anisole are most preferred. There is no specific limitation on the reaction temperature, but relatively low temperatures are preferably adopted so as to avoid side-reactions. Ordinarily, the reaction temperature is between $-10°$ C. and room temperature. The reaction time varies depending mainly on the reaction temperature and kind of the starting compounds. Generally, the period of time is between about 30 minutes and one hour.

In order to remove the protecting group forming an amide such as o-benzosulphimide by treating with a base, the compound of the formula (IV) is brought into contact with an aqueous solution of an alkali metal bicarbonate such as sodium hydrogencarbonate and potassium hydrogencarbonate in the presence or absence of an appropriate organic solvent. There is no specific limitation on the solvent, so far as it does not participate in the reaction. Preferred are tetrahydrofuran, dioxane and mixtures of these solvents and water. There is no specific limitation on the reaction temperature, but relatively low temperatures are preferably adopted so as to avoid side-reactions. Ordinarily, the reaction temperature is between $0°$ C. and room temperature. The reaction time varies depending mainly on the reaction temperature and kind of the starting compounds. Generally, the period of time is about 1–5 hours.

After completion of the reaction, the desired compound of the formula (I) is taken out of the reaction mixture in the conventional manner. The procedure of the acid treatment is, for instance, as follows. After completion of the reaction, the solvent is distilled off from the reaction mixture. To the residue are added an aqueous solution of a weak base such as dipotassium hydrogenphosphate and an organic solvent immiscible with water so that the desired compound is extracted into the aqueous layer. The aqueous layer is made acidic and extracted with an appropriate organic solvent. The solvent is then evaporated to leave the desired compound. The obtained compound may be further purified, if necessary, by the conventional method such as recrystallization, reprecipitation and chromatography.

The compound of the formula (I) which is obtained in the above-mentioned procedure may be converted into its salt in the conventional manner.

The compound of the formula (II) which is employed as the starting compound in the process of the present invention is a novel one, and can be prepared, for instance, as follows.

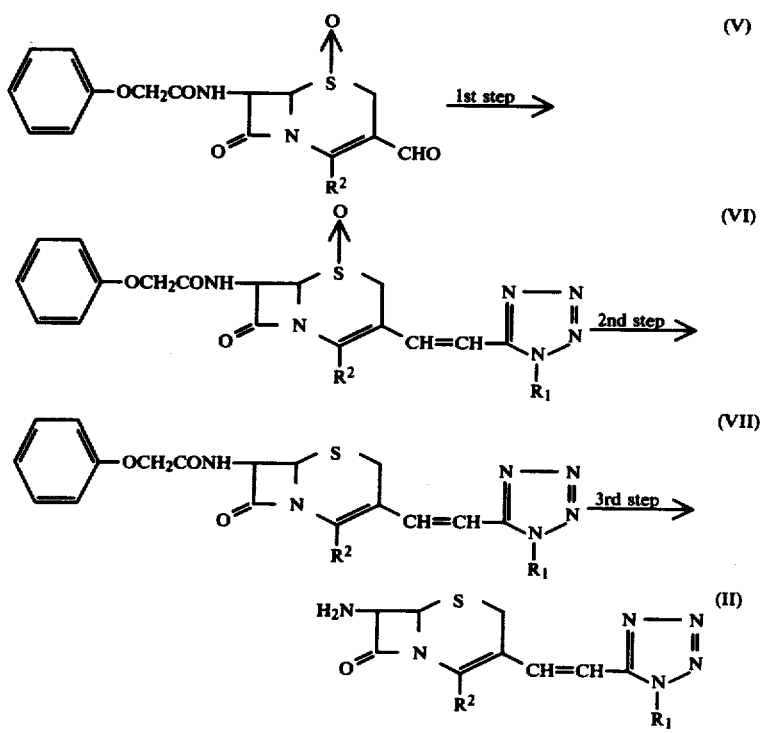

In the above formulae, $R^1$ and $R^2$ have the same meanings as defined hereinbefore.

Each step shall be explained below.

The first step is directed to the preparation of a compound of the formula (VI) and performed by reacting a known compound of the formula (V) with a Wittig reagent of the formula

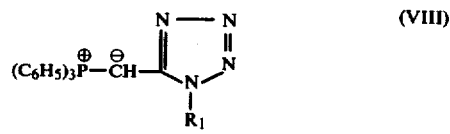

in which $R^1$ has the same meaning as defined hereinbefore. The present reaction is generally called Wittig reaction and carried out in a solvent in the conventional manner.

The second step is directed to the preparation of a compound of the formula (VII) and performed by reducing the compound of the formula (VI). The present reaction is carried out in a solvent by employing a reducing agent in the conventional manner. For instance, the reaction is preferably performed by employing potassium iodide or sodium iodide in the presence of acetyl chloride, or by employing stannous chloride, phosphorus tribromide or phosphorus trichloride.

The third step is directed to the preparation of a compound of the formula (II) and performed by removing the phenoxyacetyl group of the compound of the formula (VII). The present reaction is based on the so-called iminohalide-iminoether method which is generally utilized in the art. Accordingly, the reaction is carried out by treating in a solvent the compound of the formula (VII) with phosphorus pentachloride in the presence of quinoline to prepare an iminochloride derivative, treating the resultant with n-propanol, and treating the obtained iminoether derivative with water.

In the 1-3 steps, each of the desired compounds is obtained by treating the reaction mixture in the conventional manner after completion of the reaction. The desired compound thus obtained may be further purified, if necessary, by the conventional method such as recrystallization, reprecipitation and chromatography. In addition, the compound of the formula (II) obtained above may be, if desired, converted to an acid addition salt such as hydrohalogenic acid salt, e.g. hydrochloride and hydrobromide.

The process of this invention will be further concretely explained by examples and reference examples. However, the present invention is not limited to the examples.

EXAMPLE 1

7-(2-Thienylacetamido)-3-(1-methyl-1H-tetrazol-5-yl)vinyl-3-cephem-4-carboxylic acid

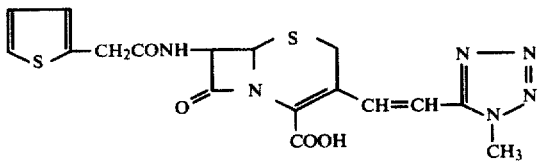

(a) In 15 ml of tetrahydrofuran was dissolved 204 mg of benzhydryl 7-amino-3-(1-methyl-1H-tetrazol-5-yl)vinyl-3-cephem-4-carboxylate hydrochloride. The solution was cooled with a freezing mixture, and to this was added with stirring 149 mg of N,N-diethylaniline. Subsequently, 77 mg of 2-thienylacetyl chloride in 2 ml of tetrahydrofuran was added dropwise to the mixture, and the resulting mixture was then stirred for one hour. After completion of the reaction, an appropriate amount of ethyl acetate was added to the reaction mixture. The mixture was then washed successively with an aqueous potassium hydrogensulfate solution, an aqueous sodium hydrogencarbonate solution and water and dried over anhydrous sodium sulfate. Upon evaporation of the solvent, there was obtained 180 mg of benzhydryl 7-(2-thienylacetamido)-3-(1-methyl-1H-tetrazol-5-yl)vinyl-3-cephem-4-carboxylate. The obtained crude product was purified by silica gel preparative chromatography (20×20×0.2 cm) with ethyl acetate as the developing solvent to yield a pure product as a pale yellow powder.

IR spectrum $\nu_{max}^{KBr}$ cm$^{-1}$: 1780, 1720.

NMR spectrum δ ppm (CDCl$_3$): 3.55 (2H, broad peak), 3.77 (2H, singlet), 3.80 (3H, singlet), 4.96 (1H, doublet) 5.80–6.05 (1H, doublet/doublet), 6.40, 8.05 (each 1H, doublet, J=16 cps), 6.93 (2H, doublet), 6.95 (1H, singlet), 7.1–7.6 (12H, multiplet).

(b) In 3 ml of dichloroethane was dissolved 100 mg of the product obtained above, and 0.5 ml of trifluoroacetic acid was added with stirring to the solution under cooling to −12° C. (inner temperature). The resulting mixture was stirred for 60 minutes. After completion of the reaction, the solvent was distilled off at room temperature under reduced pressure. The residue was dissolved in ethyl acetate and extracted with two portions of 10 ml of 10% aqueous potassium hydrogensulfate solution. The extract was washed with ethyl acetate and adjusted to pH 2 with 10% hydrochloric acid. The precipitated carboxylic acid was then extracted with ethyl acetate. The extract was dried over anhydrous sodium sulfate. Upon evaporation of the solvent, there was obtained 50 mg of 7-(2-thienylacetamido)-3-(1-methyl-1H-tetrazol-5-yl)vinyl-3-cephem-4-carboxylic acid as powdery crystals.

IR spectrum $\nu_{max}^{KBr}$ cm$^{-1}$: 3300, 1780, 1720.

NMR spectrum δ ppm (DMSO-d$_6$): 3.78 (2H, singlet), 4.08 (3H, singlet), 5.24 (1H, doublet), 5.76 (1H, quartet), 7.00, 7.90 (each 1H, doublet), 6.8–7.4 (3H, multiplet), 9.19 (1H, doublet).

EXAMPLE 2

7-D(−)-Mandelamido-3-(1-methyl-1H-tetrazol-5-yl)vinyl-3-cephem-4-carboxylic acid

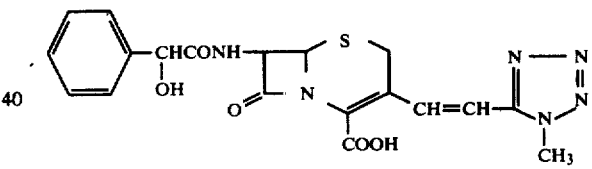

(a) Benzhydryl 7-D(−)-dichloroacetylmandelamido-3-(1-methyl-1H-tetrazol-5-yl)vinyl-3-cephem-4-carboxylate In 15 ml of anhydrous tetrahydrofuran was dissolved 204 mg of benzhydryl 7-amino-3-(1-methyl-1H-tetrazol-5-yl)vinyl-3-cephem-4-carboxylate hydrochloride. After cooling to −10° C., to this solution were added 149 mg of N,N-diethylaniline in 2 ml of tetrahydrofuran and 168.9 mg of D(−)-dichloroacetylmandelyl chloride in 2 ml of tetrahydrofuran. The mixture was then stirred at −5°-10° C. for 30 minutes. After completion of the reaction, the reaction mixture was treated in the same manner as in Example 1—(a) to give benzhydryl 7-D(−)-dichloroacetylmandelamido-3-(1-methyl-1H-tetrazol-5-yl)vinyl-3-cephem-4-carboxylate quantitatively.

IR spectrum $\nu_{max}^{KBr}$ cm$^{-1}$: 1780, 1720–1680.

NMR spectrum δ ppm (CDCl$_3$): 3.46 (2H, broad peak), 3.78 (3H, singlet), 4.94 (1H, doublet), 5.65–5.95 (1H), 6.11 (1H, singlet), 6.20 (1H, singlet), 6.93 (1H, singlet), 7.1–7.7 (16H, multiplet).

(b) In 10 ml of dichloroethane was dissolved 287 mg of the product obtained above, and the mixture was cooled to −10° C. To the mixture was then added with stirring 1.2 ml of trifluoroacetic acid, and the mixture was stirred for additional 30 minutes. After completion of the reaction, the solvent was distilled off to leave a residue. An appropriate amount of ethyl acetate was added to the residue, and the resulting solution was extracted with two portions of 20 ml of 10% aqueous dipotassium hydrogenphosphate solution. The extract was stirred for one hour under ice-cooling, adjusted to pH 2.3 with 0.5 N hydrochloric acid and extracted with ethyl acetate. This extract was then dried over anhydrous sodium sulfate. Upon evaporation of the solvent under reduced pressure, there was obtained 155 mg of 7-D(—)-mandelamido-3-(1-methyl-1H-tetrazol-5-yl)vinyl-3-cephem-4-carboxylic acid.

IR spectrum $\nu_{max}^{KBr}$ cm$^{-1}$: 3400, 3350, 1790, 1715, 1680.

NMR spectrum δ ppm (CD$_3$OD): 3.61–4.10 (2H, quartet), 4.09 (3H, singlet), 5.14 (1H, singlet), 5.17 (1H, doublet), 5.78 (1H, doublet), 6.84, 8.11 (each 1H, doublet (J=16 cps)), 7.2–7.6 (5H, multiplet).

In acetone was dissolved 100 mg of the product thus obtained, and to the solution was added an equivalent of sodium 2-ethylhexanoate in n-butanol. The mixture was diluted with ether to give a precipitate. The precipitate was collected by filtration to yield 100 mg of sodium 7-D(—)-mandelamido-3-(1-methyl-1H-tetrazol-5-yl)vinyl-3-cephem-4-carboxylate.

IR spectrum $\nu_{max}^{KBr}$ cm$^{-1}$: 1790.

EXAMPLE 3

7-(3-Isoxazolylthio)acetamido-3-(1-methyl-1H-tetrazol-5-yl)vinyl-3-cephem-4-carboxylic acid

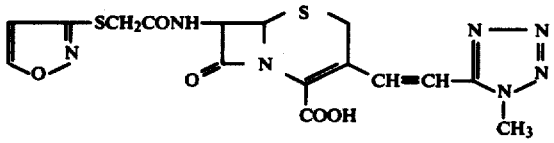

(a) Benzhydryl 7-(3-isoxazolylthio)acetamido-3-(1-methyl-1H-tetrazol-5-yl)vinyl-3-cephem-4-carboxylate In 4 ml of anhydrous tetrahydrofuran were dissolved 140 mg of benzhydryl 7-amino-3-(1-methyl-1H-tetrazol-5-yl)vinyl-3-cephem-4-carboxylate and 44 mg of N,N-diethylaniline. Under cooling to −10° C., to the solution was added with stirring 52.2 mg of 3-isoxazolylthioacetyl chloride, and the mixture was stirred for 30 minutes. After completion of the reaction, the reaction mixture was then treated in the same manner as in Example 1—(a) to give 100 mg of benzhydryl 7-(3-isoxazolylthio)acetamido-3-(1-methyl-1H-tetrazol-5-yl)vinyl-3-cephem-4-carboxylate as a yellow powder.

IR spectrum $\nu_{max}^{CHCl_3}$ cm$^{-1}$: 3140, 1783, 1720, 1690.

NMR spectrum δ ppm (CDCl$_3$): 3.42, 3.74 (each 1H, doublet), 3.84 (3H, singlet), 4.97 (1H, doublet), 5.86 (1H, quartet), 6.25 (1H, doublet), 6.50, 7.96 (each 1H, doublet, J=16 cps), 7.05–7.56 (10H, multiplet), 7.73 (1H, doublet), 8.28 (1H, doublet).

(b) In 1 ml of methylene chloride was dissolved 67 mg of the product obtained above. To the solution was added at 0° C., 0.7 ml of trifluoroacetic acid, and the mixture was stirred for 30 minutes. After completion of the reaction, the solvent and trifluoroacetic acid were both distilled off at 10° C. under reduced pressure. The residue thus obtained was then treated in the same manner as in Example 1—(b) to give 7-(3-isoxazolylthio)acetamido-3-(1-methyl-1H-tetrazol-5-yl)vinyl-3-cephem-4-carboxylic acid. The product was purified by developing it with a butanol—acetic acid—water (4:1:1) mixture by the use of silica gel thin layer chromatography (20×20×0.2 cm) to yield 22 mg of a pale yellow powder, m.p. 150°–154° C. (decomp.).

IR spectrum $\nu_{max}^{Nujol}$ cm$^{-1}$: 3400, 1780, 1724, 1680.

NMR spectrum δ ppm (DMSO-d$_6$): 3.64, 4.10 (each 1H, doublet), 3.94 (3H, singlet), 4.08 (2H, singlet), 5.22 (1H, doublet), 5.74 (1H, quartet), 6.67 (1H, doublet), 6.96, 7.91 (each 1H, doublet), 8.90 (1H, doublet).

EXAMPLE 4

7-Cyanomethylthioacetamido-3-(1-methyl-1H-tetrazol-5-yl)vinyl-3-cephem-4-carboxylic acid

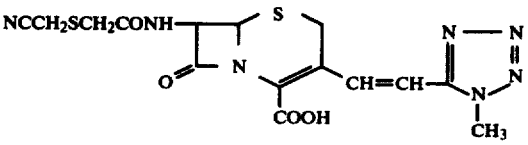

(a) Benzhydryl 7-cyanomethylthioacetamido-3-(1-methyl-1H-tetrazol-5-yl)vinyl-3-cephem-4-carboxylate To 244 mg of benzhydryl 7-amino-3-(1-methyl-1H-tetrazol-5-yl)vinyl-3-cephem-4-carboxylate in 20 ml of anhydrous tetrahydrofuran were added dropwise at −7° C. with stirring 115 mg of N,N-diethylaniline and, subsequently, 115 mg of cyanomethylthioacetyl chloride in 5 ml of anhydrous tetrahydrofuran. After completion of the reaction, the reaction mixture was then treated in the same manner as in Example 1—(a) to give a crude product. The crude product was purified by developing it with ethyl acetate by the use of silica gel thin layer chromatography (20×20×0.2 cm) to yield 50 mg of benzhydryl 7-cyanomethylthioacetamido-3-(1-methyl-1H-tetrazol-5-yl)vinyl-3-cephem-4-carboxylate.

IR spectrum $\nu_{max}^{KBr}$ cm$^{-1}$: 3300, 1800, 1720, 1680.

NMR spectrum δ ppm (DMSO-d$_6$): 3.35 (2H, singlet), 3.43 (2H, broad peak), 3.56 (2H, singlet), 3.78 (3H, singlet), 4.95 (1H, doublet), 5.84 (1H, quartet), 6.42, 8.02 (each 1H, doublet (J=16 cps)), 6.92 (1H, singlet), 7.28 (10H, broad peak), 7.70 (1H, doublet).

(b) In 2 ml of anisole was dissolved 50 mg of the product obtained above, and the solution was, after addition of 1 ml of trifluoroacetic acid at 0° C., stirred for 30 minutes. After completion of the reaction, the reaction mixture was then treated in the same manner as in Example 1—(b) to give 19 mg of 7-cyanomethylthioacetamido-3-(1-methyl-1H-tetrazol-5-yl)vinyl-3-cephem-4-carboxylic acid.

IR spectrum $\nu_{max}^{KBr}$ cm$^{-1}$: 3300, 1800, 1660–1700.

NMR spectrum δ ppm (DMSO-d$_6$): 3.46 (2H, singlet), 3.66 (2H, broad peak), 3.78 (2H, singlet), 4.06 (3H, singlet), 5.20 (1H, doublet), 5.66 (1H, quartet), 6.78, 7.98 (each 1H, doublet), 9.24 (1H, doublet).

EXAMPLE 5

7-Thienylacetamido-3-(1-methyl-1H-tetrazol-5-yl)vinyl-3-cephem-4-carboxylic acid

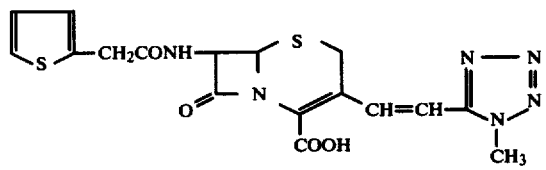

In 40 ml of water were dissolved 416 mg of 7-amino-3-(1-methyl-1H-tetrazol-5-yl)vinyl-3-cephem-4-carboxylic acid and 660 mg of sodium hydrogencarbonate. To the solution was added 10 ml of acetone and further added dropwise with stirring at 0°-5° C., 20 ml of an acetone solution containing 323 mg of 2-thienylacetyl chloride. The mixture was stirred for 30 minutes under ice-cooling and for additional 3 hours at room temperature. The acetone was distilled off at room temperature under reduced pressure. The residual solution was washed with ether, adjusted to pH 2.0 with 10% hydrochloric acid and extracted with ethyl acetate. The extract was washed with an aqueous sodium chloride solution and dried over anhydrous sodium sulfate. The ethyl acetate was removed under reduced pressure, and, upon washing the residue with ether, there was obtained 590 mg of 7-(2-thienylacetamido)-3-(1-methyl-1H-tetrazol-5-yl)vinyl-3-cephem-4-carboxylic acid.

The product thus obtained was identical with the product obtained in Example 1—(b) in IR and NMR spectra.

REFERENCE EXAMPLE 1

(1-Methyl-1H-tetrazol-5-yl)methylenetriphenylphosphorane

To 8.1 g of (1-methyl-1H-tetrazol-5-yl)methylenetriphenylphosphonium chloride in 200 ml of water was added in portions with stirring and ice-cooling 20 ml of an aqueous solution containing 804 mg of sodium hydroxide. After addition, the mixture was stirred for an additional minute and filtered at a low temperature leaving the precipitate. The precipitate was washed with ice-cooled water and immediately dried under reduced pressure to yield 5.7 g of (1-methyl-1H-tetrazol-5-yl)methylenetriphenylphosphorane.

REFERENCE EXAMPLE 2

Benzhydryl 7-phenoxyacetamido-3-(1-methyl-1H-tetrazol-5-yl)vinyl-3-cephem-4-carboxylate-1-oxide To 130 ml of anhydrous tetrahydrofuran was added 5.35 g of benzhydryl 7-phenoxyacetamido-3-formyl-3-cephem-4-carboxylate-1-oxide, and, after cooling to −5°−−10° C., further added 4.3 g of (1-methyl-1H-tetrazol-5-yl)methylenetriphenylphosphorane. The mixture was stirred at that temperature for 5 hours and poured into a mixture of ethyl acetate and ice-water. The resulting mixture was then made acidic with 10 ml of 5% hydrochloric acid. The organic layer was washed with five portions of a saturated aqueous sodium chloride solution and dried over anhydrous sodium sulfate. The solvent was distilled off under reduced pressure to leave a solid residue. The residue was, after addition of approximately 30 ml of methanol, stirred at room temperature for 20 minutes and filtered leaving a precipitate. There was obtained 3.62 g of benzhydryl 7-phenoxyacetamido-3-(1-methyl-1H-tetrazol-5-yl)vinyl-3-cephem-4-carboxylate-1-oxide as a crystalline powder. The filtrate was evaporated under reduced pressure to dryness, and the obtained residue was developed through silica gel column with ethyl acetate to give 600 mg of the crystals additionally.

IR spectrum $\nu_{max}^{Nujol}$ cm$^{-1}$: 3300, 1790, 1720, 1660.

REFERENCE EXAMPLE 3

Benzhydryl 7-phenoxyacetamido-3-(1-methyl-1H-tetrazol-5-yl)vinyl-3-cephem-4-carboxylate To 1.3 g of benzhydryl 7-phenoxyacetamido-3-(1-methyl-1H-tetrazol-5-yl)vinyl-3-cephem-4-carboxylate-1-oxide in 25 ml of N,N-dimethylformamide were added with stirring under cooling with a freezing mixture 2.0 g of potassium iodide and 0.7 ml of acetyl chloride, and the mixture was stirred for 5 minutes. The mixture was then stirred for another 90 minutes at room temperature and poured into ice-water. The separating oil was extracted with ethyl acetate. The extract was washed with an aqueous potassium metabisulfite solution, water, a dilute aqueous sodium hydrogencarbonate solution and water successively and dried over anhydrous sodium sulfate. The solvent was removed under reduced pressure to leave a residue. The obtained residue was developed through silica gel column with a mixture of benzene and ethyl acetate (1:1) to give 1.1 g of benzhydryl 7-phenoxyacetamido-3-(1-methyl-1H-tetrazol-5-yl)vinyl-3-cephem-4-carboxylate.

REFERENCE EXAMPLE 4

Benzhydryl 7-amino-3-(1-methyl-1H-tetrazol-5-yl)vinyl-3-cephem-4-carboxylate

To 15 ml of chloroform was added 1.218 g of phosphorus pentachloride, and the phosphorus pentachloride was dissolved therein by warming. To the solution maintained at 10°-20° C. was added 0.929 g of quinoline. Five minutes later, the temperature was lowered to −10°−−20° C., and to the mixture was added 2.7 g of benzhydryl 7-phenoxyacetamido-3-(1-methyl-1H-tetrazol-5-yl)vinyl-3-cephem-4-carboxylate. The mixture was then stirred for 10 minutes and at room temperature for one hour. The mixture was then cooled to 0° C., and to this was added 5.4 ml of n-propanol. The resulting mixture was stirred at room temperature for one hour and poured into ice-water. To this was further added an appropriate amount of chloroform. The precipitated crystals were collected by filtration and dried to yield 1.3 g of benzhydryl 7-amino-3-(1-methyl-1H-tetrazol-5-yl)vinyl-3-cephem-4-carboxylate hydrochloride. To the obtained hydrochloride was added a mixture of a dilute aqueous sodium hydrogencarbonate solution and ethyl acetate, and the ethyl acetate layer was separated. From the ethyl acetate layer, there was obtained the 7-amino base.

IR spectrum $\nu_{max}^{Nujol}$ cm$^{-1}$: 3400, 3340, 1780, 1720.

What is claimed is:

1. 7-D(−)mandelamido-3-(1-methyl-1H-tetrazol-5-yl)vinyl-3-cephem-4-carboxylic acid.